(12) United States Patent
Chu et al.

(10) Patent No.: US 8,642,267 B2
(45) Date of Patent: Feb. 4, 2014

(54) BIOMARKER FOR DIAGNOSIS OF CANINE CANCER

(75) Inventors: Rea-Min Chu, Taipei (TW); Han-Jung Lei, Taipei (TW); Yi-Lun Chiang, Taipei (TW)

(73) Assignee: National Taiwan University, Taipei (TW)

( * ) Notice: Subject to any disclaimer, the term of this patent is extended or adjusted under 35 U.S.C. 154(b) by 448 days.

(21) Appl. No.: 12/953,855

(22) Filed: Nov. 24, 2010

(65) Prior Publication Data

US 2011/0275081 A1 Nov. 10, 2011

(30) Foreign Application Priority Data

May 4, 2010 (TW) .............................. 99114230 A

(51) Int. Cl.
*C12Q 1/68* (2006.01)
(52) U.S. Cl.
USPC ........................................ 435/6.12; 536/23.2
(58) Field of Classification Search
None
See application file for complete search history.

(56) References Cited

PUBLICATIONS

Chu et al. (Cancer Prevention Research, 2010, vol. 3(issue 1, sup. 1): Abstract B58, presented AACR Dec. 6-9, 2009, IDS reference).*
Abruzzo et al. (Biotechniques, 2005, 38:785-792).*
Gilmore et al. (Accession No. Z70044 Apr. 2005).*
Lowe et al. (Nucleic Acids Research, 1990, 18(7):1757-1761).*
Reamin Chu et al., Gene expression study on a highly aggressive canine transmissible venereal tumor of a NOD/SCID mice model, Frontiers in Cancer Prevention Research 2009: Conference Program and Proceedings, Dec. 6-9, 2009, pp. 125.

* cited by examiner

*Primary Examiner* — Stephanie K Mummert
(74) *Attorney, Agent, or Firm* — WPAT, P.C.; Anthony King

(57) ABSTRACT

The present invention is related to a biomarker for diagnosis of canine cancer, wherein the biomarker is KMO (kynureinie 3-monooxygenase) gene, and the canine cancers including CTVT (canine transmissible venereal tumor) and MGT (mammary gland tumor). The expression level of KMO gene in canine malignant tumor tissues is up-regulated as compared with benign tissues. Furthermore, the expression level of KMO gene in malignant tumor tissue is higher than in the non-metastasis tumor tissue. By detection of the expression level of the present invention biomarker in suspecting tissue specimen, malignancy of tumor tissues can be determined correctly and rapidly.

6 Claims, 9 Drawing Sheets

CTVT  XCTVT MCTVT

The first primer

The second primer

β-actin

KMO

SEQUENCE LISTING

```
<160> NUMBER OF SEQ ID NOS: 62

<210> SEQ ID NO 1
<211> LENGTH: 20
<212> TYPE: DNA
<213> ORGANISM: Artificial sequence
<220> FEATURE:
<223> OTHER INFORMATION: RT-PCR primer of APOC-1

<400> SEQUENCE: 1
tctccccctt gaagaactga                                                       20

<210> SEQ ID NO 2
<211> LENGTH: 20
<212> TYPE: DNA
<213> ORGANISM: Artificial sequence
<220> FEATURE:
<223> OTHER INFORMATION: RT-PCR primer of APOC-1

<400> SEQUENCE: 2
acagaaccac caccaaaacc                                                       20

<210> SEQ ID NO 3
<211> LENGTH: 20
<212> TYPE: DNA
<213> ORGANISM: Artificial sequence
<220> FEATURE:
<223> OTHER INFORMATION: RT-PCR primer of LOC478576

<400> SEQUENCE: 3
atgaacgtcc tggaagatgc                                                       20

<210> SEQ ID NO 4
<211> LENGTH: 20
<212> TYPE: DNA
<213> ORGANISM: Artificial sequence
<220> FEATURE:
<223> OTHER INFORMATION: RT-PCR primer of LOC478576

<400> SEQUENCE: 4
caaatctggg gctgatcact                                                       20

<210> SEQ ID NO 5
<211> LENGTH: 20
<212> TYPE: DNA
<213> ORGANISM: Artificial sequence
<220> FEATURE:
<223> OTHER INFORMATION: RT-PCR primer of MMP-1

<400> SEQUENCE: 5
aacggacttc aggctgctta                                                       20

<210> SEQ ID NO 6
<211> LENGTH: 20
<212> TYPE: DNA
<213> ORGANISM: Artificial sequence
<220> FEATURE:
<223> OTHER INFORMATION: RT-PCR primer of MMP-1
```

```
<400> SEQUENCE: 6
aacggacttc aggctgctta                                              20

<210> SEQ ID NO 7
<211> LENGTH: 20
<212> TYPE: DNA
<213> ORGANISM: Artificial sequence
<220> FEATURE:
<223> OTHER INFORMATION: RT-PCR primer of FARS2

<400> SEQUENCE: 7
gtgtctccaa aggccatcat                                              20

<210> SEQ ID NO 8
<211> LENGTH: 20
<212> TYPE: DNA
<213> ORGANISM: Artificial sequence
<220> FEATURE:
<223> OTHER INFORMATION: RT-PCR primer of FARS2

<400> SEQUENCE: 8
gatttgccca gcagctctac                                              20

<210> SEQ ID NO 9
<211> LENGTH: 20
<212> TYPE: DNA
<213> ORGANISM: Artificial sequence
<220> FEATURE:
<223> OTHER INFORMATION: RT-PCR primer of LXN

<400> SEQUENCE: 9
aaggtgttcc aggtgcagac                                              20

<210> SEQ ID NO 10
<211> LENGTH: 20
<212> TYPE: DNA
<213> ORGANISM: Artificial sequence
<220> FEATURE:
<223> OTHER INFORMATION: RT-PCR primer of LXN

<400> SEQUENCE: 10
cagctgtgca gttcagggta                                              20

<210> SEQ ID NO 11
<211> LENGTH: 20
<212> TYPE: DNA
<213> ORGANISM: Artificial sequence
<220> FEATURE:
<223> OTHER INFORMATION: RT-PCR primer of DOCK1

<400> SEQUENCE: 11
cataggcctg tgtcagagca                                              20

<210> SEQ ID NO 12
<211> LENGTH: 20
<212> TYPE: DNA
<213> ORGANISM: Artificial sequence
<220> FEATURE:
<223> OTHER INFORMATION: RT-PCR primer of DOCK1

<400> SEQUENCE: 12
tccgggtttt tctctccttt                                              20

<210> SEQ ID NO 13
<211> LENGTH: 20
```

-continued

```
<212> TYPE: DNA
<213> ORGANISM: Artificial sequence
<220> FEATURE:
<223> OTHER INFORMATION: RT-PCR primer of SMARCC2

<400> SEQUENCE: 13
gacctggatg aacaggagga                                              20

<210> SEQ ID NO 14
<211> LENGTH: 20
<212> TYPE: DNA
<213> ORGANISM: Artificial sequence
<220> FEATURE:
<223> OTHER INFORMATION: RT-PCR primer of SMARCC2

<400> SEQUENCE: 14
tctgctcagt cacgttgtcc                                              20

<210> SEQ ID NO 15
<211> LENGTH: 20
<212> TYPE: DNA
<213> ORGANISM: Artificial sequence
<220> FEATURE:
<223> OTHER INFORMATION: RT-PCR primer of JAM3

<400> SEQUENCE: 15
cgtgaatctc aagtccagca                                              20

<210> SEQ ID NO 16
<211> LENGTH: 20
<212> TYPE: DNA
<213> ORGANISM: Artificial sequence
<220> FEATURE:
<223> OTHER INFORMATION: RT-PCR primer of JAM3

<400> SEQUENCE: 16
ggggtcagtc gtctgtgaat                                              20

<210> SEQ ID NO 17
<211> LENGTH: 20
<212> TYPE: DNA
<213> ORGANISM: Artificial sequence
<220> FEATURE:
<223> OTHER INFORMATION: RT-PCR primer of RBP4

<400> SEQUENCE: 17 gcctcttct gcaggacaac                                               20

<210> SEQ ID NO 18
<211> LENGTH: 20
<212> TYPE: DNA
<213> ORGANISM: Artificial sequence
<220> FEATURE:
<223> OTHER INFORMATION: RT-PCR primer of RBP4

<400> SEQUENCE: 18
tgcacacacg tcccagttat                                              20

<210> SEQ ID NO 19
<211> LENGTH: 20
<212> TYPE: DNA
<213> ORGANISM: Artificial sequence
<220> FEATURE:
<223> OTHER INFORMATION: RT-PCR primer of LOC476453

<400> SEQUENCE: 19
gacaagggcg agtttcagac                                              20
```

-continued

```
<210> SEQ ID NO 20
<211> LENGTH: 20
<212> TYPE: DNA
<213> ORGANISM: Artificial sequence
<220> FEATURE:
<223> OTHER INFORMATION: RT-PCR primer of LOC476453

<400> SEQUENCE: 20
caggatggcg gtaaagaaga                                                   20

<210> SEQ ID NO 21
<211> LENGTH: 20
<212> TYPE: DNA
<213> ORGANISM: Artificial sequence
<220> FEATURE:
<223> OTHER INFORMATION: RT-PCR primer of KMO

<400> SEQUENCE: 21
catgccatag tgccctttt                                                    20

<210> SEQ ID NO 22
<211> LENGTH: 20
<212> TYPE: DNA
<213> ORGANISM: Artificial sequence
<220> FEATURE:
<223> OTHER INFORMATION: RT-PCR primer of KMO

<400> SEQUENCE: 22
atggcatggt catctggaat                                                   20

<210> SEQ ID NO 23
<211> LENGTH: 20
<212> TYPE: DNA
<213> ORGANISM: Artificial sequence
<220> FEATURE:
<223> OTHER INFORMATION: RT-PCR primer of CCDC98

<400> SEQUENCE: 23
aaaaaggctg tggttggttg                                                   20

<210> SEQ ID NO 24
<211> LENGTH: 20
<212> TYPE: DNA
<213> ORGANISM: Artificial sequence
<220> FEATURE:
<223> OTHER INFORMATION: RT-PCR primer of CCDC98

<400> SEQUENCE: 24
ttcctggctt gaaagatgct                                                   20

<210> SEQ ID NO 25
<211> LENGTH: 20
<212> TYPE: DNA
<213> ORGANISM: Artificial sequence
<220> FEATURE:
<223> OTHER INFORMATION: RT-PCR primer of LOC475851

<400> SEQUENCE: 25
gggcttccag agcttctttt                                                   20

<210> SEQ ID NO 26
<211> LENGTH: 20
<212> TYPE: DNA
<213> ORGANISM: Artificial sequence
<220> FEATURE:
<223> OTHER INFORMATION: RT-PCR primer of LOC475851
```

<400> SEQUENCE: 26
ttcttgccct tctgcttcat                                               20

<210> SEQ ID NO 27
<211> LENGTH: 20
<212> TYPE: DNA
<213> ORGANISM: Artificial sequence
<220> FEATURE:
<223> OTHER INFORMATION: RT-PCR primer of SLC6A6

<400> SEQUENCE: 27
acaaaagcct gtggatcacc                                               20

<210> SEQ ID NO 28
<211> LENGTH: 20
<212> TYPE: DNA
<213> ORGANISM: Artificial sequence
<220> FEATURE:
<223> OTHER INFORMATION: RT-PCR primer of SLC6A6

<400> SEQUENCE: 28
gggtcgtcaa ttccagaaga                                               20

<210> SEQ ID NO 29
<211> LENGTH: 20
<212> TYPE: DNA
<213> ORGANISM: Artificial sequence
<220> FEATURE:
<223> OTHER INFORMATION: RT-PCR primer of FKBP15

<400> SEQUENCE: 29
aaaagcagca ccctctacga                                               20

<210> SEQ ID NO 30
<211> LENGTH: 20
<212> TYPE: DNA
<213> ORGANISM: Artificial sequence
<220> FEATURE:
<223> OTHER INFORMATION: RT-PCR primer of FKBP15

<400> SEQUENCE: 30
ctgtgtgatt ccccaggact                                               20

<210> SEQ ID NO 31
<211> LENGTH: 20
<212> TYPE: DNA
<213> ORGANISM: Artificial sequence
<220> FEATURE:
<223> OTHER INFORMATION: RT-PCR primer of GPATCH4

<400> SEQUENCE: 31
aagaggagaa agcggtcaca                                               20

<210> SEQ ID NO 32
<211> LENGTH: 20
<212> TYPE: DNA
<213> ORGANISM: Artificial sequence
<220> FEATURE:
<223> OTHER INFORMATION: RT-PCR primer of GPATCH4

<400> SEQUENCE: 32
cttcttgggc ttcttgttgc                                               20

<210> SEQ ID NO 33
<211> LENGTH: 20

-continued

```
<212> TYPE: DNA
<213> ORGANISM: Artificial sequence
<220> FEATURE:
<223> OTHER INFORMATION: RT-PCR primer of HTR7

<400> SEQUENCE: 33
agcatcatct ccctgaatgg                                                  20

<210> SEQ ID NO 34
<211> LENGTH: 20
<212> TYPE: DNA
<213> ORGANISM: Artificial sequence
<220> FEATURE:
<223> OTHER INFORMATION: RT-PCR primer of HTR7

<400> SEQUENCE: 34
tcctttcgtg cttgaggagt                                                  20

<210> SEQ ID NO 35
<211> LENGTH: 20
<212> TYPE: DNA
<213> ORGANISM: Artificial sequence
<220> FEATURE:
<223> OTHER INFORMATION: RT-PCR primer of HYI

<400> SEQUENCE: 35
acccccagta cttcctggac                                                  20

<210> SEQ ID NO 36
<211> LENGTH: 20
<212> TYPE: DNA
<213> ORGANISM: Artificial sequence
<220> FEATURE:
<223> OTHER INFORMATION: RT-PCR primer of HYI

<400> SEQUENCE: 36
cggatgtttc ctgtcaggtt                                                  20

<210> SEQ ID NO 37
<211> LENGTH: 20
<212> TYPE: DNA
<213> ORGANISM: Artificial sequence
<220> FEATURE:
<223> OTHER INFORMATION: RT-PCR primer of LOC478181

<400> SEQUENCE: 37
caaatggaca agtccgaggt                                                  20

<210> SEQ ID NO 38
<211> LENGTH: 20
<212> TYPE: DNA
<213> ORGANISM: Artificial sequence
<220> FEATURE:
<223> OTHER INFORMATION: RT-PCR primer of LOC478181

<400> SEQUENCE: 38
ccacatggat gcaatcagag                                                  20

<210> SEQ ID NO 39
<211> LENGTH: 20
<212> TYPE: DNA
<213> ORGANISM: Artificial sequence
<220> FEATURE:
<223> OTHER INFORMATION: RT-PCR primer of GNAS

<400> SEQUENCE: 39
cctttccttt tctccccaag                                                  20
```

<210> SEQ ID NO 40
<211> LENGTH: 20
<212> TYPE: DNA
<213> ORGANISM: Artificial sequence
<220> FEATURE:
<223> OTHER INFORMATION: RT-PCR primer of GNAS

<400> SEQUENCE: 40
agggaacttt tgtggccttt                                               20

<210> SEQ ID NO 41
<211> LENGTH: 20
<212> TYPE: DNA
<213> ORGANISM: Artificial sequence
<220> FEATURE:
<223> OTHER INFORMATION: RT-PCR primer of LRP1

<400> SEQUENCE: 41
catcgaagtg tccaagctca                                               20

<210> SEQ ID NO 42
<211> LENGTH: 20
<212> TYPE: DNA
<213> ORGANISM: Artificial sequence
<220> FEATURE:
<223> OTHER INFORMATION: RT-PCR primer of LRP1

<400> SEQUENCE: 42
gagtggtcac cccagtctgt                                               20

<210> SEQ ID NO 43
<211> LENGTH: 20
<212> TYPE: DNA
<213> ORGANISM: Artificial sequence
<220> FEATURE:
<223> OTHER INFORMATION: RT-PCR primer of RAB5C

<400> SEQUENCE: 43
ccaacatcgt cattgcactc                                               20

<210> SEQ ID NO 44
<211> LENGTH: 20
<212> TYPE: DNA
<213> ORGANISM: Artificial sequence
<220> FEATURE:
<223> OTHER INFORMATION: RT-PCR primer of RAB5C

<400> SEQUENCE: 44
ttgtcgtctg cataggcttg                                               20

<210> SEQ ID NO 45
<211> LENGTH: 20
<212> TYPE: DNA
<213> ORGANISM: Artificial sequence
<220> FEATURE:
<223> OTHER INFORMATION: RT-PCR primer of CCL19

<400> SEQUENCE: 45
atcccaagca gctgtgctac                                               20

<210> SEQ ID NO 46
<211> LENGTH: 20
<212> TYPE: DNA
<213> ORGANISM: Artificial sequence
<220> FEATURE:
<223> OTHER INFORMATION: RT-PCR primer of CCL19

```
<400> SEQUENCE: 46
gggttacaga aaggcagcag                                              20

<210> SEQ ID NO 47
<211> LENGTH: 20
<212> TYPE: DNA
<213> ORGANISM: Artificial sequence
<220> FEATURE:
<223> OTHER INFORMATION: RT-PCR primer of PHACTR2

<400> SEQUENCE: 47
ggagaaagtg ctttggcaag                                              20

<210> SEQ ID NO 48
<211> LENGTH: 20
<212> TYPE: DNA
<213> ORGANISM: Artificial sequence
<220> FEATURE:
<223> OTHER INFORMATION: RT-PCR primer of PHACTR2

<400> SEQUENCE: 48
atttgctgtc ggatttcctg                                              20

<210> SEQ ID NO 49
<211> LENGTH: 20
<212> TYPE: DNA
<213> ORGANISM: Artificial sequence
<220> FEATURE:
<223> OTHER INFORMATION: RT-PCR primer of LAMB2

<400> SEQUENCE: 49
atttgctgtc ggatttcctg                                              20

<210> SEQ ID NO 50
<211> LENGTH: 20
<212> TYPE: DNA
<213> ORGANISM: Artificial sequence
<220> FEATURE:
<223> OTHER INFORMATION: RT-PCR primer of LAMB2

<400> SEQUENCE: 50
tgcgtgaaat gaaactcagc                                              20

<210> SEQ ID NO 51
<211> LENGTH: 20
<212> TYPE: DNA
<213> ORGANISM: Artificial sequence
<220> FEATURE:
<223> OTHER INFORMATION: RT-PCR primer of GAPDHS

<400> SEQUENCE: 51
tgcgtgaaat gaaactcagc                                              20

<210> SEQ ID NO 52
<211> LENGTH: 20
<212> TYPE: DNA
<213> ORGANISM: Artificial sequence
<220> FEATURE:
<223> OTHER INFORMATION: RT-PCR primer of GAPDHS

<400> SEQUENCE: 52
actgtggtca tcagcccttc                                              20

<210> SEQ ID NO 53
<211> LENGTH: 20
```

```
<212> TYPE: DNA
<213> ORGANISM: Artificial sequence
<220> FEATURE:
<223> OTHER INFORMATION: RT-PCR primer of C5AR1

<400> SEQUENCE: 53
gaccgctttg tcttggtgtt                                              20

<210> SEQ ID NO 54
<211> LENGTH: 20
<212> TYPE: DNA
<213> ORGANISM: Artificial sequence
<220> FEATURE:
<223> OTHER INFORMATION: RT-PCR primer of C5AR1

<400> SEQUENCE: 54
atgaacgagg gtacggtcag                                              20

<210> SEQ ID NO 55
<211> LENGTH: 20
<212> TYPE: DNA
<213> ORGANISM: Artificial sequence
<220> FEATURE:
<223> OTHER INFORMATION: RT-PCR primer of CD5L

<400> SEQUENCE: 55
ttccagagaa tgtgcgactg                                              20

<210> SEQ ID NO 56
<211> LENGTH: 20
<212> TYPE: DNA
<213> ORGANISM: Artificial sequence
<220> FEATURE:
<223> OTHER INFORMATION: RT-PCR primer of CD5L

<400> SEQUENCE: 56
tgcaaagttc cagcttcctt                                              20

<210> SEQ ID NO 57
<211> LENGTH: 20
<212> TYPE: DNA
<213> ORGANISM: Artificial sequence
<220> FEATURE:
<223> OTHER INFORMATION: RT-PCR primer of IL18

<400> SEQUENCE: 57
atcccaagca gctgtgctac                                              20

<210> SEQ ID NO 58
<211> LENGTH: 20
<212> TYPE: DNA
<213> ORGANISM: Artificial sequence
<220> FEATURE:
<223> OTHER INFORMATION: RT-PCR primer of IL18

<400> SEQUENCE: 58
gggttacaga aaggcagcag                                              20

<210> SEQ ID NO 59
<211> LENGTH: 20
<212> TYPE: DNA
<213> ORGANISM: Artificial sequence
<220> FEATURE:
<223> OTHER INFORMATION: RT-PCR primer of VCAM1

<400> SEQUENCE: 59
ccgagcacaa ttacacatgg                                              20
```

```
<210> SEQ ID NO 60
<211> LENGTH: 20
<212> TYPE: DNA
<213> ORGANISM: Artificial sequence
<220> FEATURE:
<223> OTHER INFORMATION: RT-PCR primer of VCAM1

<400> SEQUENCE: 60
tgcagcctca tagagggagt                                          20

<210> SEQ ID NO 61
<211> LENGTH: 20
<212> TYPE: DNA
<213> ORGANISM: Artificial sequence
<220> FEATURE:
<223> OTHER INFORMATION: RT-PCR primer of B-actin

<400> SEQUENCE: 61
gatctggcac cacaccttct                                          20

<210> SEQ ID NO 62
<211> LENGTH: 20
<212> TYPE: DNA
<213> ORGANISM: Artificial sequence
<220> FEATURE:
<223> OTHER INFORMATION: RT-PCR primer of B-actin

<400> SEQUENCE: 62
acgtacatgg ttggggtgtt                                          20
```

BIOMARKER FOR DIAGNOSIS OF CANINE CANCER

BACKGROUND OF THE INVENTION

1. Field of the Invention

The present invention is related to a biomarker for detection of tumor, especially related to a biomarker for diagnosis of canine cancer.

2. The Prior Arts

Canine cancer is a common leading cause of canine death.

Canine transmissible venereal tumor (CTVT) is naturally occurring, low differentiation round tumor cells. It can be transmitted through allograft (for example, via direct tumor cell transplantation during coitus or via activities such as licking, sniffing, biting, scratching and others), wherein the tumor cells contact wounded mucous membrane or skin and consequently resulting in infection. Furthermore, experiments have demonstrated xenograft transmission. Currently, canine CTVT has been demonstrated to cross transmitted to fox, gray wolf, and immunodeficient mouse. Because this type of tumor can evolve various mechanisms to escape host immune system's monitoring and induced immune response, exhibiting unique growth curve in growth phase and natural regression phase, therefore, it is frequently used as an animal model to study tumor treatment mechanism.

Mammary gland tumor (MGT) frequently occurs in female canine, its prevalence is about 42% of all canine cancer, and is about 82% of female genatile organ derived cancer. In addition, most MGT occurs in 8 to 10 year-old female canine, while MGT in male canine is less common, if occurs, normally companion with abnormal hormone secretion. Traditionally, MGT is classified into two groups based on histopathology and cancer cytology, namely benign and malignant tumor. Benign tumor is reported to be about 40~50% of the cancer, in which its clinical characteristics include small volume, well embedded, existence for many years and slow growth. Malignant tumor is about 50~60%, and its clinical symptoms include rapid growth, no covering, ulcer or fever, lymph node invasion and transmission to remote organs, with lung as highest transmitted organs. Distant metastasis of MGT will eventually result in inhibition of organ functions or failure, which is also the main cause of canine death.

Although benignancy or malignancy of CTVT and MGT can be distinguished based on tumor characteristics, cytology and histopathology diagnosis, diagnosis by human judgment may be influence by pathologist's experience and objective opinions. A biomarker is an important tool to detect and trace human diseases as well as critical index in cancer diagnosis. However, there is rare, if any, biomarker(s) designated as tumor marker in canine tumor diagnosis in clinical application. Thus, development of rapid and correct diagnostic method and biomarker(s) will be helpful to determine if a canine is suffered with cancer.

SUMMARY OF THE INVENTION

To avoid potential bias of canine cancer diagnosis based on human judgment of histopathology or cytology test and to shorten the time required for diagnosis, the present invention provides a biomarker applied for canine tumor diagnosis, in which the biomarker is kynurenine 3-monooxygenase (KMO) gene and the canine tumor is canine transmissible venereal tumor or canine mammary gland tumor, and furthermore the results can expressed quantitatively to exhibit the expression level of malignancy so that human errors can be avoided.

In the present invention, the expression level of KMO gene in malignant mammary tumor tissue is up-regulated when compared with benign tissue; moreover the expression level of KMO gene in canine mammary tumor tissue with metastasis (i.e. at stage IV or V) is up-regulated when compared with non-metastasis tumor (e.g. at stage I, II or III).

Another purpose of the present invention is to provide a method for diagnosis of canine cancer, comprising the steps of (1) obtaining a sample from a canine subject; (2) evaluating a ratio of the expression level of the biomarker (KMO gene) to the expression level of β-actin gene in the sample, wherein evaluating the ratio comprises respectively quantifying the expression levels of the biomarker and the β-actin gene using Real-time PCR; and (3) determining the sample is a malignant tumor when the ratio of step (2) is larger than 0.00085, or the sample is a malignant tumor with metastasis when the ratio of step (2) is larger than 0.004.

The step of evaluating the ratio of the present invention comprises quantifying the expression level of the KMO gene using Real-time PCR with a pair of primer consisting of SEQ ID NO:21 and SEQ ID NO:22.

The present invention employs KMO gene as a biomarker to evaluate tumor malignancy and to apply in determination of canine cancer. By using the expression level of the KMO gene to perform tumor diagnosis, the present invention not only correctly determines degree of tumor malignancy quantitatively, but also analysis time can be greatly saved. Moreover, the present invention can be applied in cancer treatment and prognosis.

The details of one or more embodiments of the invention are set forth in the description below. Other features, objects, and advantages of the invention will be apparent from the description and from the claims.

DETAILED DESCRIPTION OF THE PREFERRED EMBODIMENT

Figure 1A:
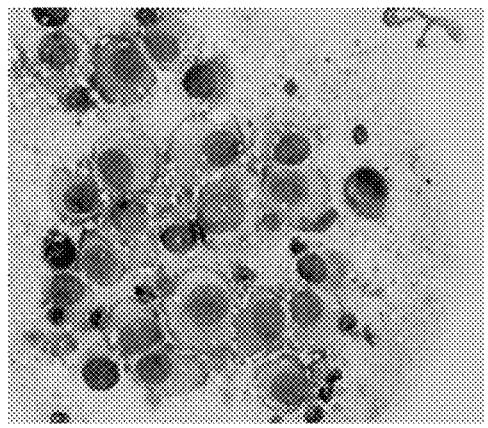
FIG. 1A is a cytological analysis of XCTVT of an embodiment of the present invention.

To identify the gene(s) that can be selected as biomarker for diagnosis of canine cancer, the present invention firstly established various animal models of canine transmissible venereal tumor (CTVT), compared the characteristic differences among tumors of various models, and then identified the corresponding gene(s) that leading to the variance. The present invention furthermore applied these gene(s) of canine cancer clinically to determine the relationship between gene expression level and tumor malignancy and metastasis.

Xenographic canine transmissible venereal tumor (abbreviated as XCTVT below) obtained by inoculating CTVT in immunodeficient (NOD/SCID) mouse had the same cytology and tissue characteristics of CTVT, and it also expressed the specific LINE-c-myc gene fragment of CTVT. When the XCTVT was re-inoculated back to canine, thus obtained tumor (designated as mouse canine transmissible venereal tumor, abbreviated as MCTVT) also exhibited the same cytology and histology characteristics of CTVT and expressed the specific LINE-c-myc gene fragment, however, growth characteristics of MCTVT had changed. Comparing with CTVT, MCTVT exhibited faster growth rate, more mitotic figure, larger tumor volume (mass) and delay into tumor regression phase.

Examples of the present invention were further exemplified by analysis of gene expression levels of MCTVT and CTVT through canine gene chip. The results show that there were 136 genes in MCTVT had two-fold more expression than in CTVT, and there were the other 37 genes in MCTVT exhibited two-fold lower expression than in CTVT. For those 30 genes that show higher expression levels in MCTVT, real-time PCR (RT-PCR) was used to confirm their expression quantitatively. It was found that three genes, including matrix metalloproteinase 1 (MMP-1), apolipoprotein C-1 (APOC-1) and kynurenine 3-monooxygenase (KMO), had significant higher gene expression levels in MCTVT than in CTVT.

Real-time PCR (RT-PCR) was further applied to analyze KMO gene expression level in MGT clinically. The results show that expression level of KMO gene in benign tumor was low, while its expression level in malignant tumor was significantly increased and expressed in even higher level when the tumor was metastasis. This phenomenon indicated that KMO gene expression was positively associated with the malignancy of tumor and related to prognosis of the disease. Thus, KMO gene can be selected as a biomarker for diagnosis of benign, malignant, or metastasis status of tumor.

Example 1

Establishment of Animal Model and Cytology and Histology Analysis

The present invention was related to grow CTVT tumor in canine and mouse respectively, then re-inoculate the XCTVT of the mouse back into canine to obtain MCTVT, so as to observe and compare cytology and histology characteristics of CTVT in thus obtained animal model.

To carry out cytology analysis, first prepared single cell suspension of various tumors and then stained for visual observation. Tumor mass obtained from various animal models were cut into small pieces and placed in RPMI1640 medium (Gibco-Invitrogen, USA) supplemented with 10% bovine serum (HyClone, USA), 1% penicillin, streptomycin and amphotericin (Sigma, St. Louis, Mo., USA). Next, using a stainless mesh cloth to press the tumor mass and filtered through two-layered cheese cloth (pore size: 190 µm) to obtain single cell suspension. 8 ml of single cell suspension was overlaid onto 4 ml of 42% Percoll™ gradient (GE Healthcare Bio-Science Corp., USA) then centrifuged at 820 g at 4° C. for 30 minutes. Collected CTVT cells in the middle layer and then washed three times with suspension medium described above. Biopsy of tumor cells was stained with Diff-Quik kit (Sysmex, Japan) and nucleus/cytoplasmic ratio, intracytoplasmic vascuolization and nucleolus was observed under microscope.

For histology analysis, tumor mass excised from various animal models were cut into suitable pieces (for example, 2×2×0.5 cm), fixed in 10% buffered formalin, embedded in paraffin and then cut into 4~6 µm thick sections. Tissue sections were stained with hematoxylin and eosin (H&E stain) and then observed under microscope to evaluate cytoplasm and nucleus. Ten visual fields were randomly selected to determine mitotic index.

1. Establishment of CVTV Animal Models 10 healthy, 1~2 year-old beagles were bred according to Institutional Animal Care and Use Committee Guideline in National Taiwan University Veterinary Teaching Hospital. Tumor mass of spontaneous case of CTVT from an external genital organ of a female canine was cut, minced and filtered through a two layer stainless steel mesh (pore size: 190 µm). Cell suspension was then used as origin of transplantation.

Supernatant containing $1 \times 10^8$ viable tumor cells was injected subcutaneously into each of the 8 sites in the back of the 10 healthy beagles. Tumor sizes were measured every week with caliper and tumor volumes were determined according to the follow formulation:

$$\text{Volume } (V, \text{ unit: cm}^3) = \pi \text{ (pi)} \times \text{length } (L, \text{ unit: cm}) \times \text{Width } (W, \text{ unit: cm}) \times \text{thickness } (T, \text{ unit: cm})/4$$

Growth of CTVT tumor was divided into two phases, namely progressive phase (P-phase), and spontaneously regresses (R-phase), in which tumor size increased during P-phase and shrank at R-phase. After 6 week of inoculation (at P-phase), the tumor was inoculated into another beagle for passage.

2. Establishment of Mouse CTVT (XCTVT) Animal Model

To establish XCTVT animal model, CTVT of canine was inoculated into immunodeficient (NOD/SCID) mouse.

Supernatant containing $1 \times 10^8$ viable tumor cells from spontaneous cases of CTVT prepared as described above were injected subcutaneously into each of the 2 sites in the back of the twenty five, 4 week old mouse (purchased from experimental Animal Center of National Taiwan University Medical Hospital). When the tumor was grown to the size larger than 2 cm in diameter, the mouse was sacrificed, and the tumor was re-inoculated into another NOD/SCID mouse for second passage.

XCTVT was injected into mouse at specific site, and no distant metastasis was observed. After three weeks of inoculation, tumor mass was grown to a size that could be touched on the body surface of the transplanted mouse, and the tumor did not enter into R-phase.

3. Establishment of Animal Models of MCTVT by Re-Inoculation of XCTVT into Canine Applying the same CTVT transplantation method described above, supernatant of $1 \times 10^8$ viable tumor cells from XCTVT case of NOD/SCID mouse after two sequential passages was injected into subcutaneous sites of beagles for another subculture to obtain MCTVT.

CTVT and MCTVT tumor tissues in P-phase and R-Phase were surgically excised under sterile condition. XCTVT tumor tissues were also surgically excised under sterile condition after the mouse was sacrificed. Tumor cytology and histology were analyzed according to methods described above. The results were shown in FIGS. 1A to 1C and FIGS. 2A to 2C.

Figure 1B:
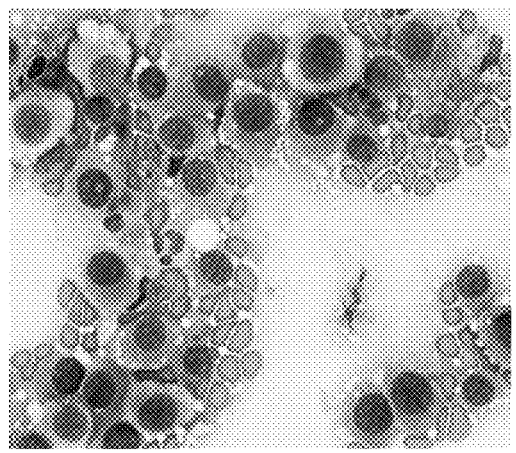
FIG. 1B is a cytological analysis of MCTVT of an embodiment of the present invention.
Figure 1C:
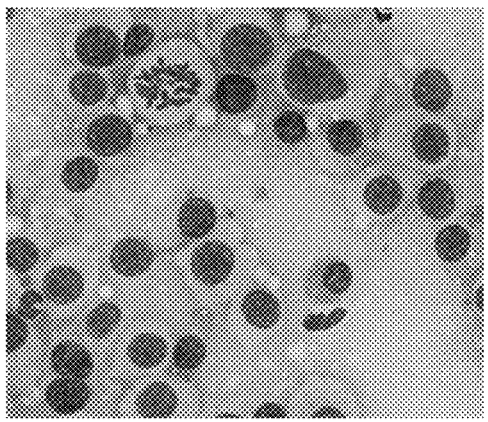
FIG. 1 C is a cytological analysis of CTVT of an embodiment of the present invention.

Referring to FIGS. 1A, 1B and 1C, these Figs show the results of cytology analysis of XCTVT, MCTVT, and CTVT of the present invention. From these figures, it could be observed that cytology characteristics of XCTVT and MCTVT were similar to that of CTVT, however, intracytoplasmic vacuolization of XCTVT and MCTVT were more obvious than that of CTVT.

Figure 2A:
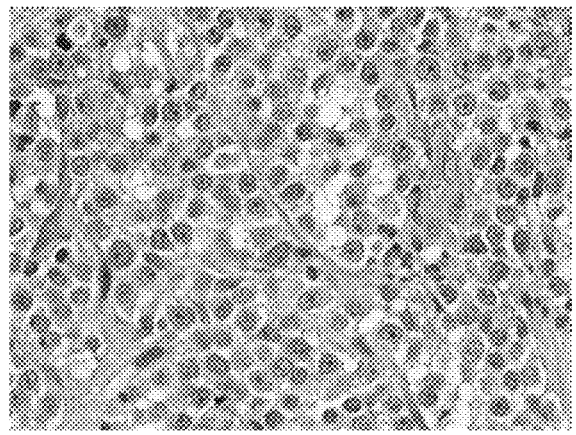
FIG. 2A is a histological analysis of CTVT of the embodiment of the present invention. Original magnification: ×400.
Figure 2B:
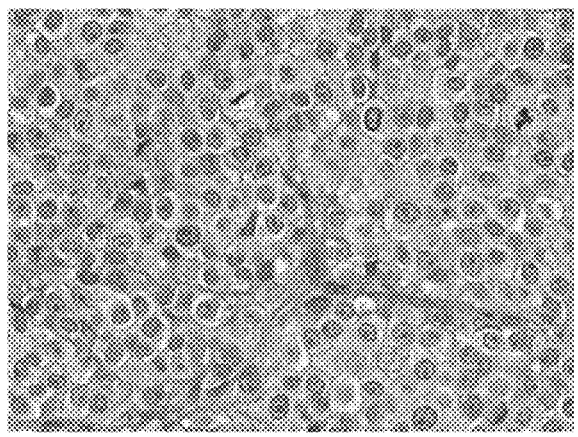
FIG. 2B is a histological analysis of XCTVT of the embodiment of the present invention. Original magnification: ×400.
Figure 2C:
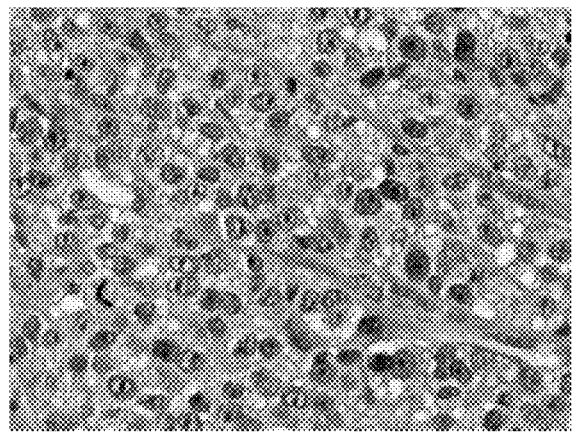
FIG. 2C is a histological analysis of MCTVT of the embodiment of the present invention. Original magnification: ×400.

Referring to FIGS. 2A, 2B and 2C, these figures show the results of histology analysis of XCTVT, MCTVT, and CTVT of the present invention. From these figures, it was found that XCTVT, MCTVT, and CTVT all contained round, oval or polyhedral cells, with chromatin clumping and a big nucleolus. In addition, mitotic figure of these tumors were all normal, and mitotic figure in XCTVT and MCTVT were more than in CTVT, in which mitotic figure observed in XCTVT, MCTVT, and CTVT was $50\pm7.81$, $32\pm2.65$ and $19.33\pm1.53$, respectively. Overall, there was no significant difference statistically in histology analysis among XCTVT, MCTVT and CTVT.

Figure 3:
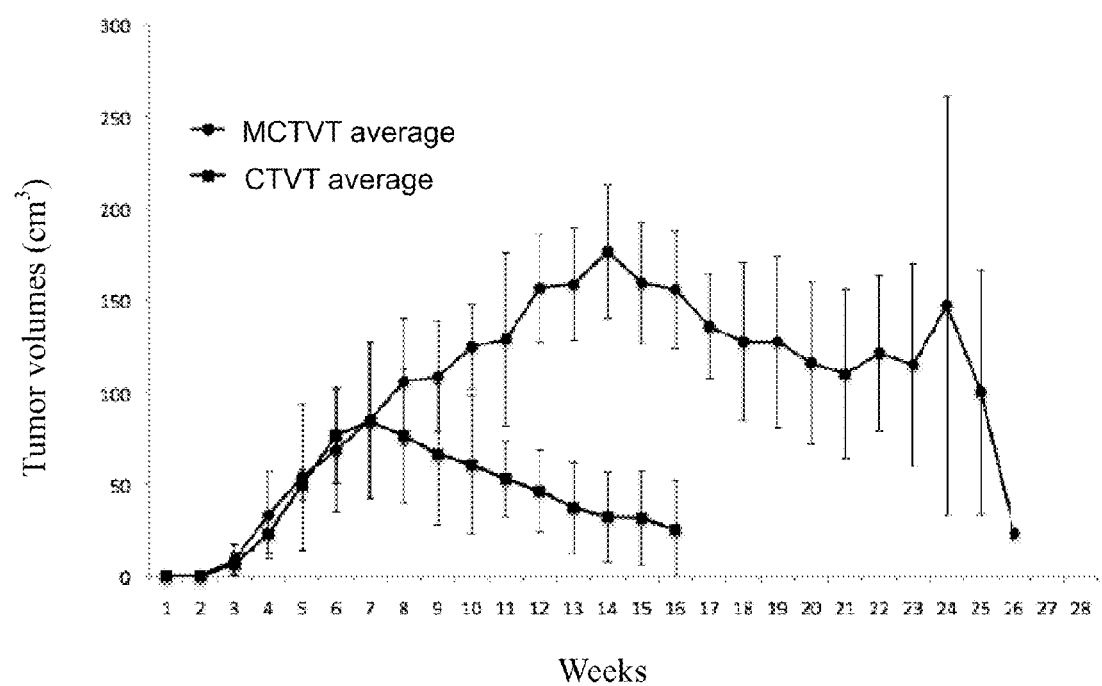
FIG. 3 are the results of tumor growth of MCTVT and CTVT of the embodiment of the present invention.

Referring to FIG. 3 was MCTVT and CTVT growth according to a embodiment of the present invention. This figure shows that logarithmic growth phase of MCTVT was significantly longer than that of CVTV, tumor size of MCTVT was larger than that of CTVT, and tumor growth of MCTVT was faster than that of CTVT. From the characteristics of tumor growth it was known that MCTVT belonged to the highly aggressive tumor group with greater malignancy than that of CTVT.

On the other hand, two primers of prior arts were applied to carry out PCR test to examine if tumors expressed the specific LINE/c-myc gene fragment of CTVT, in which the gene sequence of the first primer was based on the publication of Choi et al. (Choi, Y., Ishiguro, N., Shinagawa, M., Kim, C. J., Okamoto, Y., Minami, S., Ogihara, K., 1999, Molecular structure of canine LINE-1 elements in canine transmissible venereal tumor. Anim Genet 30, 51-53.) and the gene sequence of the second primer was based on the publication of Liao et al. (Liao, K. W., Lin, Z. Y., Pao, H. N., Kam, S. Y., Wang, F. I., Chu, R. M., 2003b, Identification of canine transmissible venereal tumor cells using in situ polymerase chain reaction and the stable sequence of the long interspersed nuclear element. J Vet Diagn Invest 15, 399-406.). Furthermore, the β-actin was designed as the housekeeping gene. The results were shown in FIG. 4, expression of LINE/c-myc gene could be detected in XCTVT, MCTVT and CTVT.

Example 2

Selection of Biomarkers for CTVT Diagnosis

Although MCTVT and CTVT had similar cytological and histological characteristics and MCTVT could express LINE/c-myc gene fragment of CTVT, MCTVT tumor growth exhibited high aggressiveness. To compare variation in gene expression between MCTVT and CTVT and to determine the cause that triggers malignancy of MCTVT, the present invention used GeneChip® Canine Genome 2.0 microarray to analyze and compare gene expression in MCTVT and CTVT.

1. Analysis and Comparison of Gene Expression in MCTVT and CTVT

To perform RNA extraction, examples of the present invention used TRIzol reagent and the extraction method followed the prior publications (Wang et al., 2009) and manufacturer's protocol.

CTVT and MCTVT tumor tissues in P-phase and R-Phase were surgically excised under sterile condition. Tissue specimens were ground and suspended in TRIzol reagent. Vortex then placed at room temperature for 10 minutes. After chloroform extraction, RNA was precipitated with isopropanol. The RNA precipitate was collected by centrifugation then washed with 70% ethanol. Ethanol was air dried and the RNA was re-dissolved in diethylpyrocarbonate-treated water (DEPC-water). Quality of RNA extract was examined and measured at 260 nm using biophotometer (Eppendorf, Germany). Total RNA was further purified using RNeasy mini kit (Qiagen, Valencia, Calif., USA) and ready for further Affymetrix gene chip analysis.

Oligonucleotide microarray analysis was followed. GeneChip® Canine Genome 2.0 Array (Affymetrix, Santa Clara, Calif., USA) was used to assess mRNA expression of the present invention. The microarray contained 42,860 canine probe sets and could detect more than 20,000 genes. First, 8 μg of total RNA prepared as described above was reverse transcribed to cDNA using a T7-$(dT)_{24}$ primer with One-cycle cDNA Synthesis kit (Affymetrix). Synthesized cDNA was purified and transcribed with biotin-labeled ribonucleotide (IVT Labeling kit; Affymetrix); The biotin-labeled RNA was then fragmented (containing more than or less than 200 nucleotides), heated at 99° C. for 5 minutes, and hybridized with GeneChip® Canine Genome 2.0 Array at 45° C. for 16 hours. Then the microarray was washed, stained with dye following the manufacturer's protocol, and then scanned with Affymetrix GeneChip Scanner 3000. The level of gene expression was analyzed by Affymetrix GeneChip Operating Software, Version 1.4. Probe pairs were used as positive or negative control to compare perfect pairing or un-pairing of probe imaging. Results of difference in gene expression level were analyzed by Principal Component Analysis (PCA), One-way analysis of Variance (ANOVA) and Hierarchical Clustering Method. The results were shown in FIG. 5.

Figure 5:
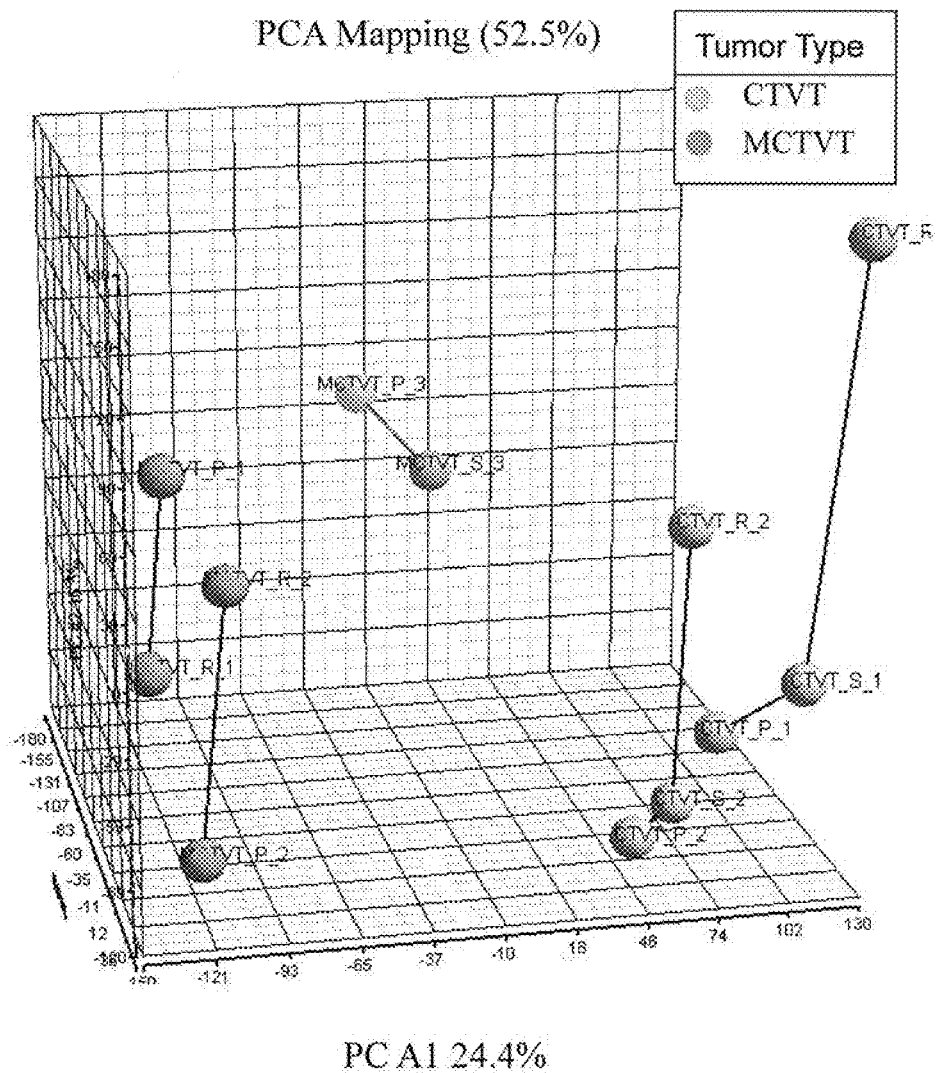
FIG. 5 illustrated the PCA evaluation results of gene expression differences in CTVT and MCTVT.

Referring to FIG. 5, this figure shows difference of gene expression of CTVT and MCTVT using PCA evaluation method. PCA was a method that applied instrument to read gene expression level on the microarray then converts and reflects the reading values into a 3D principle component graph. By comparison of various gene positions in the 3D space, difference in gene expression levels could be evaluated. Using PCA analysis, gene expression level of CTVT and MCTVT could be divided into two groups, suggesting that there were significant difference in CTVT and MCTVT tumor gene expression.

In addition, ANOVA analysis indicated that there was significant differences ($p<0.00005$) in expression levels of 998 genes between CTVT and MCTVT. On the other hand, group analysis also demonstrated that significant difference in expression levels of 998 genes between CTVT and MCTVT.

Based on three criteria (1) genes differing in expression level show at least 2 times fold change; (2) gene expression signal must be higher than 100; and (3) the gene was found in all chip tested, 173 genes in total that exhibited difference in gene expression were identified in CTVT and MCTVT tumor tissues at P-phase (referring to Table 1 and Table 2). CP value (CTVT P-phase signal) represented expression level of various genes in CTVT tumor tissue at P-phase, and MP value was the expression level of genes in MCTVT tumors at P-Phase. MP/CP ratio was the fold change of gene expression in MCTVT and CTVT.

Among these 173 genes, there were 136 genes of MCTVT expression levels higher than CTVT, that is, these genes were up-regulated and their differences were larger than two folds (referring to Table 1). There were 37 genes of MCTVT expression levels significantly lower than CTVT, meaning these genes were down-regulated, and the differences were larger than two folds (referring to Table 2).

TABLE 1

136 genes up-regulated in MCTVT

| Probe Set Name | Gene Smbol | Entrez Gene NO | CP value | MP value | MP/CP ratio |
|---|---|---|---|---|---|
| Cfa.8843.1.A1_at | APOC-1 | 476437 | 390.40 | 2379.00 | 6.09 |
| Cfa.10996.1.A1_at | LOC480665 | 480665 | 172.15 | 924.10 | 5.37 |
| Cfa.8843.1.A1_s_at | APOC-1 | 476437 | 270.60 | 1385.50 | 5.12 |
| Cfa.11513.1.S1_at | ERH | 480371 | 217.55 | 1108.80 | 5.10 |
| CfaAffx.17453.1.S1_x_at | LOC478576 | 478576 | 388.70 | 1950.05 | 5.02 |
| CfaAffx.18130.1.S1_at | LOC608732 | 608732 | 571.55 | 2732.20 | 4.78 |
| CfaAffx.23166.1.S1_at | MMP-1 | 489428 | 354.75 | 1429.40 | 4.03 |
| Cfa.20468.1.S1_at | OTUD5 | 480911 | 140.30 | 522.15 | 3.72 |
| CfaAffx.2038.1.S1_x_at | LOC475077 | 475077 | 1725.00 | 6410.50 | 3.72 |
| Cfa.15947.1.A1_at | USP13 | 478640 | 127.10 | 459.65 | 3.62 |
| Cfa.12478.1.S1_at | GPR177 | 611491 | 583.55 | 2061.80 | 3.53 |
| Cfa.17131.1.S1_at | FARS2 | 488204 | 179.65 | 633.40 | 3.53 |
| Cfa.14007.1.A1_x_at | LXN | 610062 | 148.60 | 503.20 | 3.39 |
| CfaAffx.20305.1.S1_at | DOCK1 | 486934 | 134.25 | 452.20 | 3.37 |
| Cfa.16860.1.S1_at | SMARCC2 | 481107 | 118.10 | 389.85 | 3.30 |
| CfaAffx.15462.1.S1_x_at | LOC474501 | 474501 | 4421.80 | 14574.40 | 3.30 |
| CfaAffx.15393.1.S1_at | JAM3 | 489271 | 149.65 | 492.10 | 3.29 |
| Cfa.15489.1.S1_at | RBP4 | 477775 | 705.20 | 2277.00 | 3.23 |
| CfaAffx.8543.1.S1_at | LOC476453 | 476453 | 146.75 | 470.20 | 3.20 |
| Cfa.14036.1.A1_at | KMO | 480093 | 280.95 | 883.70 | 3.15 |
| CfaAffx.12626.1.S1_at | MICAL2 | 476858 | 338.75 | 1063.95 | 3.14 |
| CfaAffx.9544.1.S1_s_at | LOC483360 | 483360 | 198.45 | 617.70 | 3.11 |
| CfaAffx.14398.1.S1_at | CCDC98 | 478459 | 119.00 | 369.25 | 3.10 |
| CfaAffx.16895.1.S1_at | PDCD4 | 477818 | 134.55 | 414.45 | 3.08 |
| CfaAffx.21051.1.S1_x_at | LOC478212 | 476799 | 185.95 | 567.30 | 3.05 |
| Cfa.11612.1.S1_at | UBE4A | 479418 | 3947.80 | 11993.90 | 3.04 |
| CfaAffx.345.1.S1_x_at | LOC486372 | 486372 | 197.65 | 599.30 | 3.03 |
| Cfa.13772.1.A1_x_at | LOC475851 | 475851 | 2206.00 | 6684.25 | 3.03 |
| CfaAffx.9885.1.S1_at | LOC476183 | 476183 | 181.20 | 545.20 | 3.01 |
| CfaAffx.7662.1.S1_s_at | SLC6A6 | 404000 | 215.90 | 630.95 | 2.92 |
| Cfa.14047.1.A1_at | ELAC1 | 476197 | 159.70 | 463.50 | 2.90 |
| CfaAffx.5753.1.S1_at | FKBP15 | 481677 | 288.25 | 827.55 | 2.87 |
| CfaAffx.23166.1.S1_s_at | MMP-1 | 489428 | 493.40 | 1404.35 | 2.85 |
| CfaAffx.25660.1.S1_at | GPATCH4 | 480121 | 122.05 | 346.75 | 2.84 |
| Cfa.3997.1.A1_at | HTR7 | 477762 | 117.90 | 332.25 | 2.82 |
| CfaAffx.8726.1.S1_s_at | HYI | 482531 | 108.75 | 306.00 | 2.81 |
| Cfa.4208.1.S1_at | LOC478181 | 478181 | 945.35 | 2659.60 | 2.81 |
| Cfa.5692.1.A1_x_at | GNAS | 403943 | 1622.25 | 4519.85 | 2.79 |
| Cfa.8070.1.A1_at | LOC475191 | 475191 | 288.30 | 801.75 | 2.78 |
| CfaAffx.16112.1.S1_at | LOC488054 | 488054 | 392.55 | 1062.95 | 2.71 |
| Cfa.17009.1.S1_at | LRP1 | 481124 | 212.95 | 553.95 | 2.60 |
| Cfa.3802.1.S1_s_at | RAB5C | 403941 | 248.80 | 647.20 | 2.60 |
| Cfa.15809.1.S1_at | CCL19 | 448793 | 183.40 | 476.55 | 2.60 |
| CfaAffx.1410.1.S1_s_at | PHACTR2 | 476230 | 139.25 | 360.85 | 2.59 |
| Cfa.20623.1.S1_s_at | LAMB2 | 476626 | 151.80 | 392.45 | 2.59 |
| CfaAffx.9682.1.S1_s_at | FMNL2 | 476151 | 133.05 | 343.90 | 2.58 |
| Cfa.245.1.S1_at | LOC479778 | 479778 | 173.65 | 445.90 | 2.57 |
| CfaAffx.28854.1.S1_s_at | JUN | 609429 | 153.20 | 390.50 | 2.55 |
| CfaAffx.11397.1.S1_at | GAPDHS | 476483 | 178.70 | 454.85 | 2.55 |
| Cfa.20474.1.S1_at | ASCC3 | 475008 | 219.00 | 546.05 | 2.49 |
| CfaAffx.9238.1.S1_at | USP36 | 483344 | 141.65 | 347.10 | 2.45 |
| Cfa.8772.1.A1_s_at | LOC478722 | 478722 | 105.05 | 257.20 | 2.45 |
| CfaAffx.30628.1.S1_s_at | SH3GLB2 | 491306 | 136.95 | 332.85 | 2.43 |
| Cfa.8336.1.A1_at | RSPH3 | 484057 | 123.10 | 296.95 | 2.41 |
| CfaAffx.25304.1.S1_s_at | LASP1 | 608624 | 206.25 | 497.35 | 2.41 |
| CfaAffx.20015.1.S1_s_at | TNK2 | 488025 | 136.95 | 329.75 | 2.41 |
| Cfa.19888.1.A1_at | CEP72 | 478632 | 364.50 | 870.15 | 2.39 |
| Cfa.1439.1.A1_at | LOC484931 | 484931 | 240.90 | 574.60 | 2.39 |
| CfaAffx.23127.1.S1_s_at | SLC23A3 | 488534 | 128.40 | 304.05 | 2.37 |
| Cfa.14652.1.A1_at | DNAJC1 | 607587 | 445.35 | 1053.05 | 2.36 |
| Cfa.12294.1.A1_at | WDR60 | 482827 | 161.00 | 378.90 | 2.35 |
| Cfa.21569.1.S1_s_at | HSPG2 | 403440 | 138.10 | 322.35 | 2.33 |
| CfaAffx.14172.1.S1_at | H3F3A | 480110 | 201.95 | 470.50 | 2.33 |
| CfaAffx.23605.1.S1_x_at | LOC479087 | 479087 | 150.90 | 351.50 | 2.33 |
| Cfa.20329.1.S1_at | PDE4DIP | 475817 | 108.90 | 253.65 | 2.33 |

TABLE 1-continued 136 genes up-regulated in MCTVT

Figure 4:
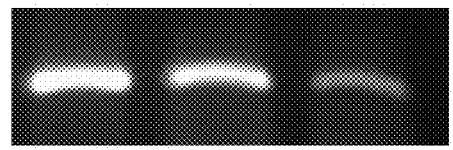
FIG. 4 shows the results of LINE/c-myc gene expression detected in XCTVT, MCTVT, and CTVT using PCR.
Figure 4:
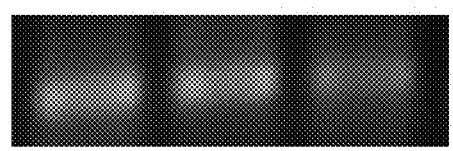
Figure 4:
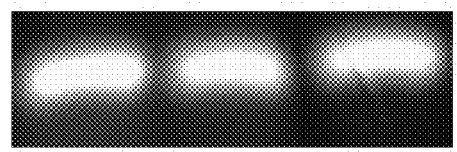

| Probe Set Name | Gene Smbol | Entrez Gene NO | CP value | MP value | MP/CP ratio |
|---|---|---|---|---|---|
| CfaAffx.13116.1.S1_at | MND1 | 482653 | 162.05 | 376.10 | 2.32 |
| Cfa.7704.1.A1_s_at | PPRC1 | 477805 | 180.65 | 417.15 | 2.31 |
| CfaAffx.30111.1.S1_at | ITFG3 | 490100 | 123.85 | 284.15 | 2.29 |
| Cfa.2263.1.A1_at | DHX29 | 478060 | 1498.65 | 3435.50 | 2.29 |
| CfaAffx.9661.1.S1_at | LOC612748 | 612748 | 204.65 | 468.70 | 2.29 |
| Cfa.3834.1.S1_at | C5AR1 | 442974 | 224.75 | 513.10 | 2.28 |
| Cfa.14036.1.A1_s_at | KMO | 480093 | 189.65 | 432.15 | 2.28 |
| CfaAffx.921.1.S1_x_at | LOC477309 | 477309 | 550.15 | 1253.15 | 2.28 |
| CfaAffx.24956.1.S1_s_at | CASP9 | 487432 | 159.65 | 363.00 | 2.27 |
| CfaAffx.15444.1.S1_s_at | NKD1 | 487288 | 163.65 | 371.65 | 2.27 |
| CfaAffx.14981.1.S1_x_at | BAP1 | 484737 | 169.75 | 384.80 | 2.27 |
| Cfa.21524.1.S1_s_at | BAT2 | 481713 | 166.20 | 376.20 | 2.27 |
| Cfa.15973.1.A1_at | KHDRBS1 | 487316 | 103.70 | 234.30 | 2.26 |
| Cfa.19709.2.S1_at | CPNE1 | 477213 | 217.05 | 489.80 | 2.26 |
| CfaAffx.24184.1.S1_at | PRAF2 | 480912 | 241.75 | 544.80 | 2.25 |
| CfaAffx.467.1.S1_at | LOC476842 | 476842 | 287.50 | 646.15 | 2.25 |
| CfaAffx.25435.1.S1_s_at | ZNF688 | 489908 | 197.80 | 443.05 | 2.24 |
| CfaAffx.15823.1.S1_at | TEX264 | 476607 | 298.50 | 666.55 | 2.23 |
| CfaAffx.6534.1.S1_at | NARG1 | 483817 | 114.95 | 256.35 | 2.23 |
| Cfa.20229.1.S1_at | LOC608502 | 608502 | 118.35 | 262.95 | 2.22 |
| CfaAffx.25378.1.S1_at | ZNF553 | 489901 | 125.05 | 277.65 | 2.22 |
| Cfa.5955.1.S1_at | CD5L | 609953 | 568.45 | 1261.60 | 2.22 |
| CfaAffx.7826.1.S1_s_at | RAB37 | 483298 | 143.55 | 318.15 | 2.22 |
| CfaAffx.24190.1.S1_at | B3GAT3 | 483785 | 188.55 | 417.45 | 2.21 |
| Cfa.20160.1.S1_at | FANCD2 | 484659 | 177.40 | 392.05 | 2.21 |
| Cfa.12122.1.A1_s_at | EMILIN1 | 475696 | 187.50 | 413.80 | 2.21 |
| Cfa.4210.2.S1_a_at | ATP5J | 478393 | 5880.00 | 12971.45 | 2.21 |
| Cfa.40.1.S1_at | IL18 | 403796 | 269.25 | 592.25 | 2.20 |
| CfaAffx.964.1.S1_x_at | LOC476842 | 476842 | 261.10 | 570.55 | 2.19 |
| Cfa.17300.1.S1_at | LOC612569 | 612569 | 175.65 | 382.65 | 2.18 |
| Cfa.10738.1.A1_a_at | RIBC1 | 480929 | 107.80 | 234.70 | 2.18 |
| Cfa.17841.1.S1_s_at | ACTN4 | 484526 | 550.70 | 1195.95 | 2.17 |
| Cfa.10174.3.S1_a_at | LOC478370 | 478370 | 2090.05 | 4529.50 | 2.17 |
| CfaAffx.17515.1.S1_at | GNG4 | 607513 | 204.75 | 443.50 | 2.17 |
| CfaAffx.29573.1.S1_s_at | PDPK1 | 479875 | 290.75 | 629.60 | 2.17 |
| Cfa.4292.2.A1_a_at | CIRBP | 476755 | 199.25 | 429.60 | 2.16 |
| CfaAffx.30417.1.S1_s_at | LOC489662 | 489662 | 178.10 | 382.05 | 2.15 |
| Cfa.268.1.A1_at | LOC610276 | 610276 | 279.45 | 597.65 | 2.14 |
| Cfa.12573.1.A1_at | FKBP15 | 481677 | 466.35 | 997.30 | 2.14 |
| CfaAffx.3512.1.S1_at | GNMT | 474905 | 195.55 | 417.95 | 2.14 |
| CfaAffx.712.1.S1_x_at | LOC485484 | 485484 | 624.25 | 1331.70 | 2.13 |
| CfaAffx.25462.1.S1_at | CD68 | 489476 | 234.05 | 498.55 | 2.13 |
| CfaAffx.24794.1.S1_s_at | JARID1C | 491894 | 124.25 | 264.55 | 2.13 |
| CfaAffx.681.1.S1_at | LOC610074 | 479513 | 321.95 | 683.40 | 2.12 |
| Cfa.18316.1.S1_s_at | RNF185 | 486362 | 183.85 | 390.25 | 2.12 |
| Cfa.16764.1.S1_at | LOC491182 | 491182 | 197.25 | 417.45 | 2.12 |
| Cfa.10933.1.A1_at | ZCRB1 | 477640 | 428.85 | 906.50 | 2.11 |
| Cfa.13491.1.A1_s_at | LOC476775 | 476775 | 354.85 | 746.50 | 2.10 |
| CfaAffx.539.1.S1_x_at | LOC490888 | 490888 | 252.20 | 528.90 | 2.10 |
| CfaAffx.3764.1.S1_s_at | UBAP2 | 481583 | 181.70 | 380.15 | 2.09 |
| CfaAffx.22768.1.S1_x_at | LOC478833 | 478833 | 112.65 | 235.40 | 2.09 |
| CfaAffx.30622.1.S1_s_at | VCAM1 | 403982 | 215.60 | 449.00 | 2.08 |
| CfaAffx.16370.1.S1_s_at | SH3PXD2A | 486874 | 121.15 | 252.10 | 2.08 |
| CfaAffx.14972.1.S1_at | LY86 | 478712 | 234.80 | 488.40 | 2.08 |
| CfaAffx.8742.1.S1_x_at | HYI | 482531 | 146.50 | 304.65 | 2.08 |
| CfaAffx.443.1.S1_x_at | LOC607796 | 607796 | 795.15 | 1652.80 | 2.08 |
| Cfa.11473.1.A1_at | B3GNT4 | 486255 | 125.70 | 260.75 | 2.07 |
| Cfa.3362.1.S1_at | DNAJC19 | 488090 | 185.50 | 384.35 | 2.07 |
| Cfa.13370.1.A1_at | CD68 | 489476 | 310.20 | 637.50 | 2.06 |
| Cfa.18579.1.S1_at | YBX2 | 489467 | 125.15 | 257.15 | 2.05 |
| CfaAffx.6706.1.S1_at | FIG4 | 475023 | 342.35 | 702.00 | 2.05 |
| Cfa.18073.1.S1_s_at | LOC485036 | 485036 | 166.00 | 339.40 | 2.04 |
| CfaAffx.6342.1.S1_s_at | SCAF1 | 484376 | 149.00 | 303.50 | 2.04 |
| Cfa.19621.1.S1_s_at | ZNFX1 | 477260 | 159.65 | 324.75 | 2.03 |
| Cfa.10600.1.A1_at | BAG5 | 480444 | 297.70 | 605.55 | 2.03 |
| Cfa.15089.1.A1_at | THRA | 403601 | 152.10 | 308.70 | 2.03 |
| Cfa.8199.1.S1_at | LOC483462 | 483462 | 176.00 | 357.40 | 2.03 |
| CfaAffx.29810.1.S1_at | TCF3 | 485079 | 180.70 | 366.75 | 2.03 |
| Cfa.3913.1.S1_at | PDGFB | 442986 | 282.65 | 572.90 | 2.03 |
| CfaAffx.25171.1.S1_at | CAPN8 | 612029 | 121.80 | 246.35 | 2.02 |
| CfaAffx.14467.1.S1_at | LOC486590 | 486590 | 149.40 | 301.30 | 2.02 |
| CfaAffx.7814.1.S1_s_at | ZNF342 | 484453 | 162.75 | 328.20 | 2.02 |
| Cfa.2777.1.A1_at | PHKG1 | 489784 | 154.70 | 311.85 | 2.02 |
| CfaAffx.30148.1.S1_s_at | QSOX2 | 607571 | 150.15 | 302.35 | 2.01 |
| Cfa.11701.1.A1_s_at | CCDC63 | 477479 | 165.80 | 333.65 | 2.01 |

TABLE 1-continued 136 genes up-regulated in MCTVT

| Probe Set Name | Gene Smbol | Entrez Gene NO | CP value | MP value | MP/CP ratio |
|---|---|---|---|---|---|
| CfaAffx.8707.1.S1_at | DNAJB6 | 608937 | 124.45 | 249.95 | 2.01 |
| CfaAffx.4668.1.S1_s_at | EPN1 | 608964 | 230.55 | 461.45 | 2.00 |
| CfaAffx.16143.1.S1_at | POLS | 488057 | 131.45 | 263.00 | 2.00 |

TABLE 2

37 genes down-regulated in MCTVT

| Probe Set Name | Gene Smbol | Entrez Gene NO | CP value | MP value | MP/CP ratio |
|---|---|---|---|---|---|
| CfaAffx.20075.1.S1_s_at | MGP | 611039 | 2715.40 | 752.25 | 0.28 |
| CfaAffx.23335.1.S1_s_at | SELL | 480080 | 1041.00 | 292.55 | 0.28 |
| Cfa.20779.1.S1_at | CXCL12 | 449622 | 983.05 | 284.15 | 0.29 |
| CfaAffx.1247.1.S1_s_at | VNN1 | 442973 | 376.60 | 114.95 | 0.31 |
| CfaAffx.15001.1.S1_s_at | SPARCL1 | 478470 | 614.35 | 193.25 | 0.31 |
| Cfa.4077.1.S1_s_at | CA4 | 480591 | 1561.45 | 495.50 | 0.32 |
| CfaAffx.13249.1.S1_at | SFRP2 | 475471 | 4655.50 | 1773.65 | 0.38 |
| CfaAffx.10230.1.S1_at | EEA1 | 475424 | 632.40 | 253.65 | 0.40 |
| CfaAffx.10118.1.S1_at | POSTN | 477298 | 4576.00 | 1841.30 | 0.40 |
| CfaAffx.24909.1.S1_s_at | EMR3 | 484900 | 278.70 | 112.60 | 0.40 |
| Cfa.1200.1.S1_s_at | SFRP2 | 475471 | 4981.75 | 2016.10 | 0.40 |
| Cfa.3510.1.S2_at | IL8 | 403850 | 1760.25 | 725.45 | 0.41 |
| Cfa.11839.1.A1_s_at | PPM2C | 477941 | 453.20 | 190.05 | 0.42 |
| CfaAffx.343.1.S1_s_at | HNRPA3 | 606946 | 2508.45 | 1056.50 | 0.42 |
| Cfa.1490.2.S1_a_at | LOC474612 | 474612 | 477.70 | 201.50 | 0.42 |
| Cfa.4556.2.S1_at | IGHAC | 480452 | 837.95 | 359.80 | 0.43 |
| CfaAffx.20848.1.S1_s_at | HNRPA3 | 608074 | 2215.20 | 976.45 | 0.44 |
| CfaAffx.12174.1.S1_s_at | EXOC6 | 477771 | 1002.20 | 443.60 | 0.44 |
| Cfa.16624.1.A1_at | USP38 | 476071 | 1046.35 | 464.05 | 0.44 |
| CfaAffx.11852.1.S1_at | IPO7 | 485383 | 2402.50 | 1080.40 | 0.45 |
| CfaAffx.24714.1.S1_at | ACBD3 | 611888 | 963.00 | 444.00 | 0.46 |
| Cfa.19918.1.S1_s_at | ZNF638 | 475799 | 436.15 | 203.00 | 0.47 |
| CfaAffx.13200.1.S1_at | NFS1 | 477214 | 406.80 | 189.65 | 0.47 |
| CfaAffx.13597.1.S1_s_at | VCAN | 488922 | 778.15 | 363.00 | 0.47 |
| Cfa.1509.3.A1_s_at | PRPF4B | 488199 | 720.90 | 339.25 | 0.47 |
| Cfa.21298.1.S1_s_at | SFRS10 | 478663 | 956.25 | 451.50 | 0.47 |
| Cfa.16472.2.S1_s_at | C1S | 486714 | 1093.45 | 517.85 | 0.47 |
| Cfa.18904.1.S1_s_at | IFI44 | 490198 | 262.40 | 124.30 | 0.47 |
| Cfa.4077.1.S1_at | CA4 | 480591 | 1900.10 | 905.80 | 0.48 |
| Cfa.20888.1.S1_s_at | ACTR2 | 481396 | 2463.25 | 1177.75 | 0.48 |
| Cfa.19109.1.S1_s_at | WDR45L | 480820 | 395.65 | 190.20 | 0.48 |
| Cfa.3850.1.S1_s_at | CAV1 | 403980 | 2209.95 | 1063.80 | 0.48 |
| Cfa.3850.1.S2_at | CAV1 | 403980 | 2706.50 | 1310.55 | 0.48 |
| Cfa.2663.1.A1_a_at | LOC475941 | 475941 | 408.85 | 199.20 | 0.49 |
| Cfa.15798.1.S1_s_at | FUT8 | 448804 | 431.05 | 210.10 | 0.49 |
| CfaAffx.18301.1.S1_s_at | RCC1 | 487332 | 853.35 | 416.80 | 0.49 |
| Cfa.11921.1.A1_at | AMICA1 | 610790 | 358.30 | 175.30 | 0.49 |
| CfaAffx.17824.1.S1_s_at | CFI | 478515 | 707.45 | 347.00 | 0.49 |
| CfaAffx.28974.1.S1_at | PPAP2B | 479557 | 649.15 | 318.70 | 0.49 |
| Cfa.15466.1.S1_s_at | SLU7 | 479308 | 664.15 | 328.00 | 0.49 |
| CfaAffx.22578.1.S1_at | SLC11A1 | 478909 | 325.85 | 162.35 | 0.50 |

2. Quantitative Analysis of Genes that Shows Difference in Expression Levels

Based on the results described above, 30 genes of MCTVT were up-regulated (as shown in Table 3). Because most of the canine gene sequences were still predictive sequences, the table was sorted by expression variation from high to low. After removal of genes that might have multiple possibilities of predictive sequences and screening of genes that had single predictive sequences, expression of 30 selected genes were further confirmed using real-time PCR.

Figure 6A:
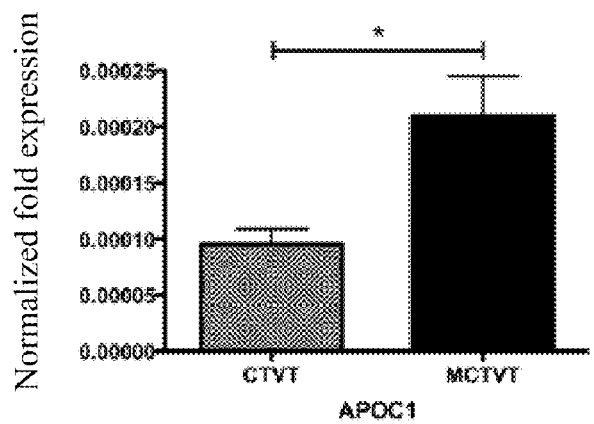
FIG. 6A exhibited the Real-Time PCR results of expression of APOC-1 gene.
Figure 6B:
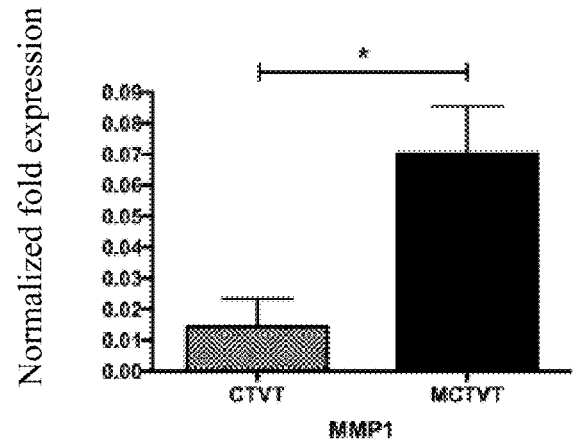
FIG. 6B exhibited the Real-Time PCR results of expression of MMP-1 gene.
Figure 6C:
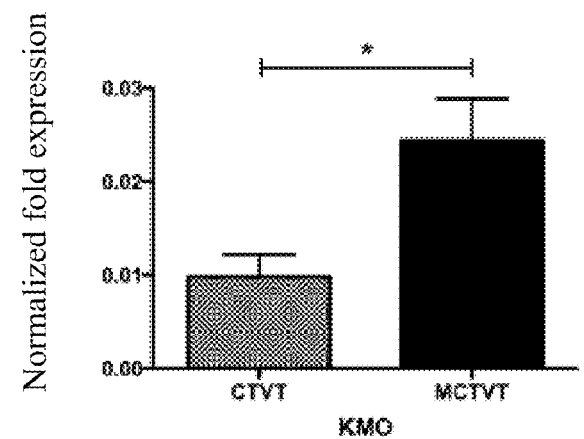
FIG. 6C exhibited the Real-Time PCR results of expression of KMO gene.

Total RNA prepared as described above was treated with DNase I (Fermentas, Canada) to remove genomic DNA. RNA was placed at 70° C. for 10 minutes for denaturation and then placed on ice for 10 minutes. 4 μl of 5× first strand buffer (Invitrogen, Carlsbad, USA), 1 μl of 10 mM dNTPs, 2 μl of 100 mM DTT (Invitrogen, USA), 1 μl of RNase-free water and 2 μl of SuperScript II reverse transcriptase (Invitrogen, USA) were added, followed by reverse transcription (42° C., 2 hours) using Mastercycler Personal. Then real-time PCR was performed with fluorescent dye (SYBER Green Master Mix) and Bio-Rad real-time PCR machine. The primers for PCR were shown in Table 3. The relative amount of mRNA of the target genes was determined by comparing to β-actin gene threshold cycle. The results were shown in FIGS. 6A to 6C.

TABLE 3

Primer sequences used for real-time PCR

| Gene Name | Entrez Gene NO | MP/CP ratio | Sense primer (5'-3') | SEQ ID NO | Anti-sense primer (5'-3') | SEQ ID NO |
|---|---|---|---|---|---|---|
| APOC-1 | 476437 | 6.09 | tctcccccttgaagaactga | 1 | acagaaccaccaccaaaacc | 2 |
| LOC478576 | 478576 | 5.02 | atgaacgtcctggaagatgc | 3 | caaatctggggctgatcact | 4 |
| MMP-1 | 489428 | 4.03 | aacggacttcaggctgctta | 5 | aacggacttcaggctgctta | 6 |
| FARS2 | 488204 | 3.53 | gtgtctccaaaggccatcat | 7 | gatttgcccagcagctctac | 8 |
| LXN | 610062 | 3.39 | aaggtgttccaggtgcagac | 9 | cagctgtgcagttcagggta | 10 |
| DOCK1 | 486934 | 3.37 | cataggcctgtgtcagagca | 11 | tccggttttttctctccttt | 12 |
| SMARCC2 | 481107 | 3.30 | gacctggatgaacaggagga | 13 | tctgctcagtcacgttgtcc | 14 |
| JAM3 | 489271 | 3.29 | cgtgaatctcaagtccagca | 15 | ggggtcagtcgtctgtgaat | 16 |
| RBP4 | 477775 | 3.23 | gcctctttctgcaggacaac | 17 | tgcacacacgtcccagttat | 18 |
| LOC476453 | 476453 | 3.20 | gacaagggcgagtttcagac | 19 | caggatggcggtaaagaaga | 20 |
| KMO | 48W93 | 3.15 | catgccatagtgcccttttt | 21 | atggcatggtcatctggaat | 22 |
| CCDC98 | 478459 | 3.10 | aaaaaggctgtggttggttg | 23 | ttcctggcttgaaagatgct | 24 |
| LOC475851 | 475851 | 3.03 | gggcttccagagcttctttt | 25 | ttcttgcccttctgcttcat | 26 |
| SLC6A6 | 404000 | 2.92 | acaaaagcctgtggatcacc | 27 | gggtcgtcaattccagaaga | 28 |
| FKBP15 | 481677 | 2.87 | aaaagcagcaccctctacga | 29 | ctgtgtgattccccaggact | 30 |
| GPATCH4 | 480121 | 2.84 | aagaggagaaagcggtcaca | 31 | cttcttgggcttcttgttgc | 32 |
| HTR7 | 477762 | 2.82 | agcatcatctccctgaatgg | 33 | tcctttcgtgcttgaggagt | 34 |
| HYI | 482531 | 2.81 | accccccagtacttcctggac | 35 | cggatgtttcctgtcaggtt | 36 |
| LOC478181 | 478181 | 2.81 | caaatggacaagtccgaggt | 37 | ccacatggatgcaatcagag | 38 |
| GNAS | 403943 | 2.79 | cctttccttttctccccaag | 39 | agggaacttttgtggccttt | 40 |
| LRP1 | 481124 | 2.60 | catcgaagtgtccaagctca | 41 | gagtggtcaccccagtctgt | 42 |
| RAB5C | 403941 | 2.60 | ccaacatcgtcattgcactc | 43 | ttgtcgtctgcataggcttg | 44 |
| CCL19 | 448793 | 2.60 | atcccaagcagctgtgctac | 45 | gggttacagaaaggcagcag | 46 |
| PHACTR2 | 476230 | 2.59 | ggagaaagtgctttggcaag | 47 | atttgctgtcggatttcctg | 48 |
| LAMB2 | 476626 | 2.59 | atttgctgtcggatttcctg | 49 | tgcgtgaaatgaaactcagc | 50 |
| GAPDHS | 476483 | 2.55 | tgcgtgaaatgaaactcagc | 51 | actgtggtcatcagcccttc | 52 |
| C5AR1 | 442974 | 2.28 | gaccgctttgtcttggtgtt | 53 | atgaacgagggtacggtcag | 54 |
| CD5L | 609953 | 2.22 | ttccagagaatgtgcgactg | 55 | tgcaaagttccagcttcctt | 56 |
| IL18 | 403796 | 2.20 | atcccaagcagctgtgctac | 57 | gggttacagaaaggcagcag | 58 |
| VCAM1 | 403982 | 2.08 | ccgagcacaattacacatgg | 59 | tgcagcctcatagagggagt | 60 |
| β-actin | — | — | gatctggcaccacaccttct | 61 | acgtacatggttggggtgtt | 62 |

The results of the embodiment of the present invention indicated that among the 30 up-regulated genes of MCTVT, wherein matrix metalloproteinase 1 (abbreviated as MMP-1), apolipoprotein C-1 (abbreviated as APOC-1), and kynuronine 3-monooxygenase (abbreviated as KMO) show two-fold higher of gene expression levels as compared with CTVT. The quantitative analysis results matched with the GeneChip test. Referred to FIGS. 6A to 6C, these Figs show up-regulation of these three genes of MCTVT described above in real-time PCR. Therefore, KMO, APOC-1 and MMP-1 could be candidate genes for diagnosis of CTVT.

Examples 3

Confirmation of Biomarkers for CTVT Diagnosis

The present invention applied real-time PCR to analyze mRNA expression of KMO gene in thirty-five canines that had infected with mammary gland tumor (MGT), and to evaluate the relationship between KMO gene expression and tumor malignancy.

Thirty-five tumor tissues from spontaneous cases of MGT (obtained from National Taiwan University Veterinary Teaching Hospital and National Chung Hsing University Veterinary Teaching Hospital) were collected. These specimens were classified as benign or malignant based on histopathology test. Clinical stages of these tumor tissues were also classified according to TMN system of World Health Organization (referring to Table 4). Among which seven MGT tissues were benign and twenty-eight tissues were malignant.

TABLE 4

Clinical stage of MGT
Clinical TNM Stage of Canine MGT

T: primary tumor

| | |
|---|---|
| T1 | <3 cm maximum diameter |
| T2 | 3~5 cm maximum diameter |
| T3 | >5 cm maximum diameter |

N: regional LN status

| | |
|---|---|
| N0 | No histological metastasis |
| N1 | Histological metastasis |

M: distant metastasis

| | |
|---|---|
| M0 | No distant metastasis detected |
| M1 | Distant metastasis detected | stage grouping

| | | | |
|---|---|---|---|
| stage I | T1 | N0 | M0 |
| stage II | T2 | N0 | M0 |
| stage III | T3 | N0 | M0 |
| stage IV | Any T | N1 | M0 |
| stage V | Any T | Any N | M1 |

Total RNA of MGT tissue was prepared as described above, and real-time PCR was performed using corresponding primers (SEQ ID: NO: 21 and SEQ ID NO: 22 as primers for KMO gene detection; SEQ ID NO: 61 (5' end primer) and SEQ ID NO: 62 (3' end primer) as primers for β-actin gene detection). The results were presented in average value and standard deviation (mean±SD). The results were shown in Table 5, FIG. 7A, FIGS. 8A and 8B, and FIG. 9.

TABLE 5

Results of Real-time PCR of KMO expression in MGT

| Tumor characteristic | Tumor number | KMO mRNA expression | $P^a$ |
|---|---|---|---|
| Age at onset | | | |
| <13 years | 16 | 0.0034 ± 0.0028 | 0.4868 |
| ≥13 years | 12 | 0.0027 ± 0.0019 | |
| Weight of Canine | | | |
| ≤10 kg | 20 | 0.0032 ± 0.0025 | 0.7649 |
| ≥10 kg | 8 | 0.0029 ± 0.0024 | |
| Tumor size | | | |
| ≤5 cm | 20 | 0.0028 ± 0.0024 | 0.3640 |
| >5 cm | 8 | 0.0039 ± 0.0028 | |
| regional LN status | | | |
| N0 | 10 | 0.0020 ± 0.0020 | 0.0001 |
| N1 | 18 | 0.0056 ± 0.0016 | |

TABLE 5-continued

Results of Real-time PCR of KMO expression in MGT

| Tumor characteristic | Tumor number | KMO mRNA expression | $P^a$ |
|---|---|---|---|
| distant metastasis | | | |
| M0 | 11 | 0.0032 ± 0.0026 | 0.1554 |
| M1 | 7 | 0.0009 ± 0.0009 | |
| Tumor stage | | | |
| I/II/III | 20 | 0.0021 ± 0.0021 | 0.0002 |
| IV/V | 8 | 0.0056 ± 0.0016 | |

$^a$Student's t-test (p value) was used for comparison, p value <0.05 indicating significant difference.

Figure 7A:
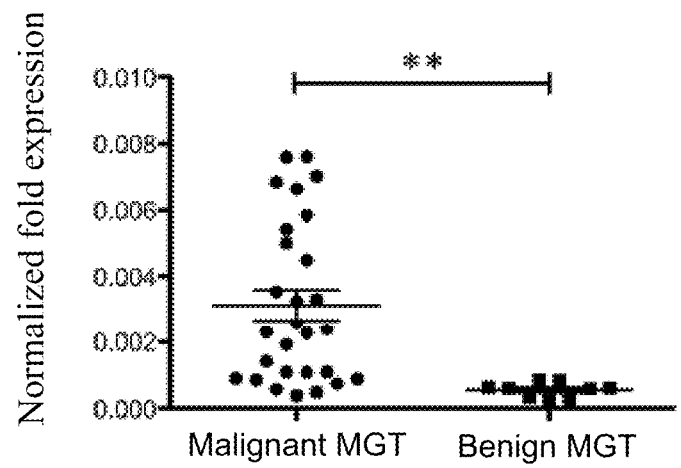
FIG. 7A shows the Real-Time PCR results of KMO gene expression in benign and malignant MGT.
Figure 7B:
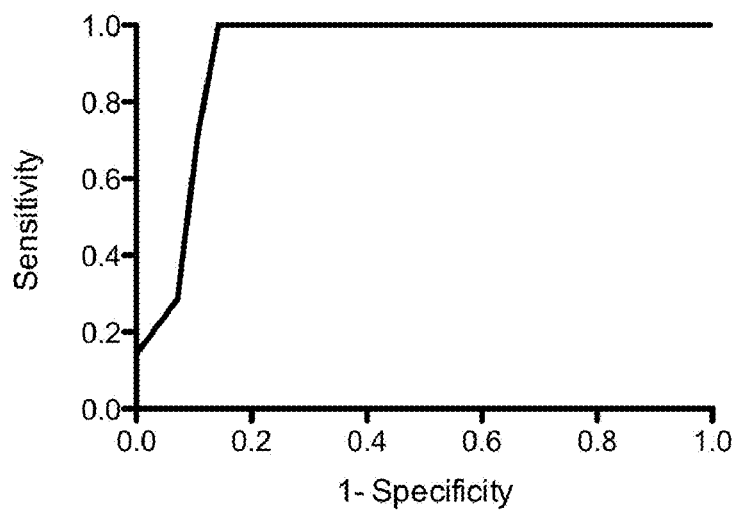
FIG. 7B illustrated the diagnosis of tumor malignancy using ROC curve to evaluate KMO gene expression.

Referring to Table 5 and FIG. 7A, the results of real-time PCR of KMO gene expression in benign and malignant MGT tumor tissue were shown. The normalized fold expression of KMO gene (i.e. KMO/β-actin ratio) was 0.0031±0.0024 in malignant tissue, while the ratio was 0.0006±0.0002 in benign tumor tissue, indicating that KMO gene expression (p=0.00006) in malignant tissue was significantly higher than in benign tissue. Plotting normalized fold expression of KMO gene in the format of Receiver Operating Characteristics (ROC) curve as shown in FIG. 7B, the cut-off point of normalized fold expression for metastasis diagnosis was 0.00085, and the sensitivity and specificity was 100% and 85.7%, respectively.

Figure 8A:
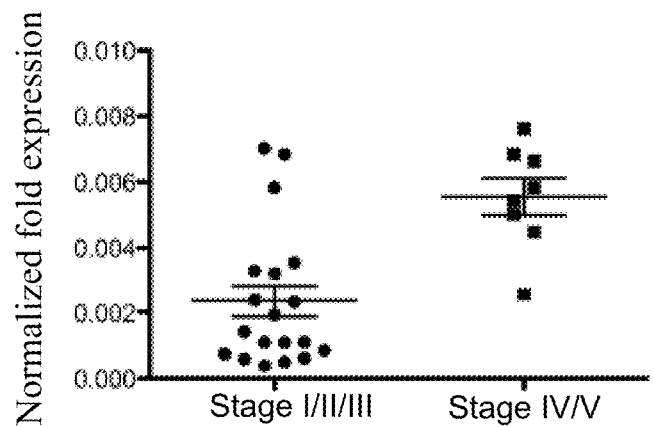
FIG. 8A shows expression level of KMO gene detected by Real-Time PCR in MGT tumor tissues from stage I/II/III to IV/V.
Figure 8B:
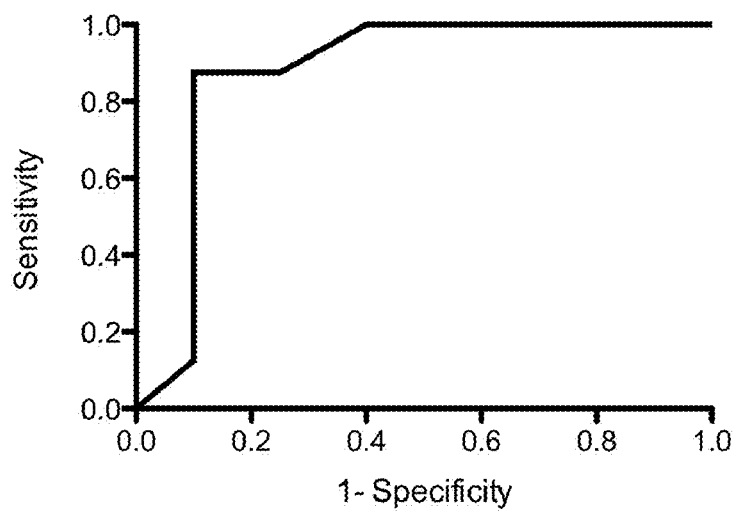
FIG. 8B shows the results of application of ROC curve analysis to assess correlation between KMO gene expression and of MGT tumor metastasis.

Referring to Table 5 and FIG. 8A, the results of Real-Time PCR of the KMO gene expression in MGT tissue tumor from stage I to V were shown. Normalized fold expression (i.e. the KMO/β-actin ratio) of KMO gene in tumors at stage I, II and III was 0.0021±0.0021, while the ratio was 0.0056±0.0016 in tumors at stage IV/V. Therefore, the results indicated that KMO gene was over expressed (p=0.0002) in tumor tissues at stage IV/V. Plotting normalized fold expression (i.e. the KMO/β-actin ratio) of KMO gene in the format of ROC curve as shown in FIG. 8B, the cut-off point of normalized fold expression for metastasis diagnosis was 0.0004, and the sensitivity and specificity was 90% and 87.5%, respectively.

Figure 9:
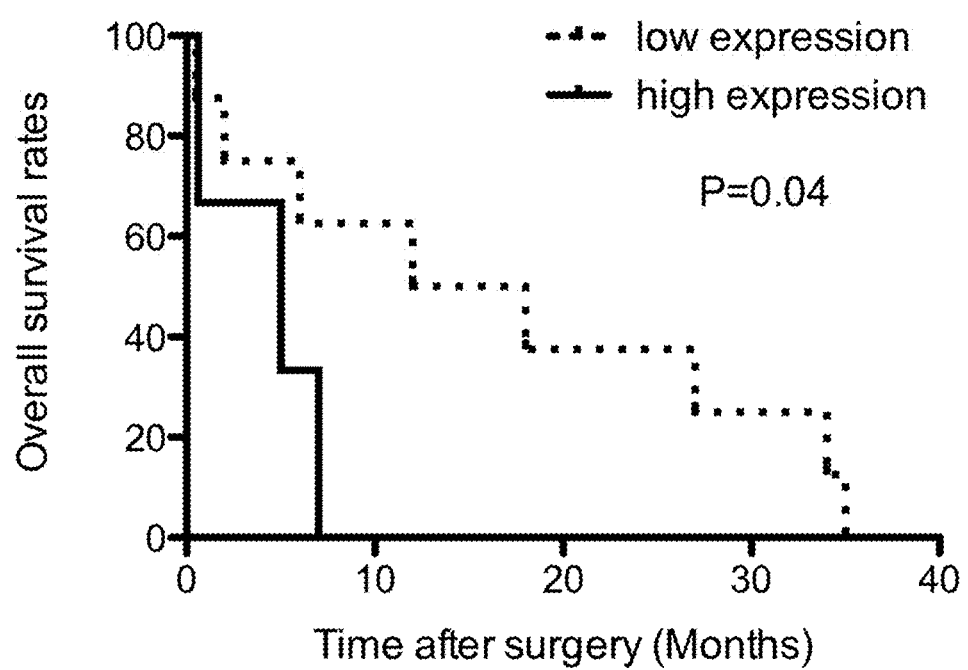
FIG. 9 shows the results of correlation between the expression level of KMO gene and the survival rate of MGT.

Referring to FIG. 9, it demonstrated Kaplan-Meier survival analysis of canine with high or low KMO gene expression. The plot was grouped by expression level of KMO gene and the cutoff value for KMO/β-actin ratio obtained from RT-PCR test was 0.0055. In this figure, KMO gene expression level is inversely associated with the survival time of canine. When the expression of KMO gene of canine suffering from MGT was low, overall survival rate was longer. On the contrary, if the expression of KMO gene of canine suffering from MGT was high, overall survival rate was shorter.

The results shown above indicated that KMO gene expression was significantly higher in malignant tissues. In the respective of tumor malignancy, it also shows that expression of KMO gene of metastatic tissues at stage IV/V was significantly higher than tumors at stage I/II/III. Furthermore, when the canine suffered with MGT exhibited high KMO gene expression, the survival rate was much lower than those canines with low KMO gene expression. Therefore, these results suggested that expression level of KMO gene was related to malignancy of canine cancer.

In conclusion, expression level of KMO gene could not only applied in identification of benign or malignant tumors, but also applied in differentiation of high aggressive tumors (metastasis) from low malignancy (non-metastasis), suggesting that KMO gene could be designated as biomarker for diagnosis of canine cancer, identification of benign/malignant tumor, and aggressiveness of malignancy.

When the biomarker of the present invention was applied in diagnosis of canine cancer, the steps of the method comprised of (1) obtaining a sample from a canine subject; (2) evaluating a ratio of the expression level of KMO gene to the expression level of β-actin gene in the sample; and (3) determining the sample is a malignant tumor when the ratio of step (2) is larger than 0.00085, or the sample is a malignant tumor with metastasis when the ratio of step (2) is larger than 0.004.

The expression level of KMO gene is determined using real-time PCR and corresponding primers consisting of SEQ ID NOS:21 and SEQ ID NO:22.

---

What is claimed is:

1. A method for diagnosis of canine cancer, comprising the steps of:
   (1) obtaining a tumor sample from a canine subject, wherein the tumor is a canine transmissible venereal tumor or canine mammary gland tumor;
   (2) measuring the gene expression level of kynurenine 3-monooxygenase (KMO) gene in the tumor sample of step (1);
   (3) measuring the gene expression level of beta-actin in the tumor sample of step (1);
   (4) establishing a ratio of the expression level of KMO in the tumor sample compared to the expression level of beta-actin in the same tumor sample; and
   (5) determining the tumor sample of step (1) is a malignant tumor when the ratio of step (4) is larger than 0.00085, or the tumor sample is a malignant tumor with metastasis when the ratio of step (4) is larger than 0.004.

2. The method of claim 1, wherein the step (3) has a sensitivity of 100% and accuracy of 85.7% for determining that the sample is a malignant tumor.

3. The method of claim 1, wherein the step (3) has a sensitivity of 90% and accuracy of 85.7% for determining that the sample is a malignant tumor with metastasis.

4. The method of claim 1, wherein evaluating the ratio comprises respectively quantifying the expression levels of the biomarker and the β-actin gene using Real-time PCR with a pair of primer.

5. The method of claim 4, wherein the pair of primer for quantifying the expression level of the biomarker consisting of SEQ ID NOS:21 and SEQ ID NO:22.

6. The method of claim 4, wherein the pair of primer for quantifying the expression level of β-actin gene consisting of SEQ ID NOS:61 and SEQ ID NO:62.

* * * * *